US00PP12410P2

(12) United States Plant Patent
Zaiger et al.

(10) Patent No.: US PP12,410 P2
(45) Date of Patent: Feb. 12, 2002

(54) PEACH TREE NAMED 'MAY SWEET'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/316,054

(22) Filed: May 21, 1999

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Annette H. Para

(57) ABSTRACT

A new and distinct variety of peach tree (*Prunus persica*); the features of the tree and its fruit are characterized with the tree budded on Nemaguard Rootstock (non-patented), grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization. The tree consists of the following unique combination of desirable features that are outstanding in a new variety:

1. Fruit ripening in the early maturity season.
2. Fruit with firm flesh and good handling and shipping quality.
3 Mild, sweet, sub-acid fruit with excellent flavor and eating quality.
4. Fruit with a high degree of attractive red skin color.
5. Relatively uniform fruit throughout the tree.
6. Vigorous, upright growth.

1 Drawing Sheet

BACKGROUND OF THE VARIETY

In the field of plant genetics, we conduct an extensive and continuing plant-breeding program including the organization and asexual reproduction of orchard trees, of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peaches and nectarines known to us, and mentioned herein; Fayette Peach (non-patented), Royal April Peach (U.S. Plant Pat. No. 3,411), May Crest Peach (U.S. Plant Pat. No. 4,064), May Grand Nectarine (U.S. Plant Pat. No. 2,794) and Sweet Gem Peach (U.S. Plant Pat. No. 7,952).

ORIGIN OF THE VARIETY

The present new variety of peach tree was originated by us in our experimetal orchard located near Modesto, Calif., as a first generation cross between two selected seedlings with field identification numbers 36EB85 and 5GE8. The maternal parent 36EB85 (non-patented) was selected as an addition to our gene pool to be used in our fruit breeding program and originated from an open pollinated seedling selected from a cross between May Grand Nectarine (U.S. Plant Pat. No. 2,794) with a peach of unknown parentage. The paternal parent 5GE8 (non-patented) was selected as an addition to our gene pool to be used in our breeding program and originated as a selected seedling from a cross between Fayette Peach (non-patented) with Royal April Peach (U.S. Plant Pat. No. 3,411) which was then crossed with May Crest Peach (U.S. Plant Pat. No. 4,064). A large group of these first generation seedlings were planted and maintained under close observation by us, in May of 1992 we recognized the desirable fruit characteristics described above and selected the present variety, growing on its own root, for asexual reproduction and commercialization.

ASEXUAL REPRODUCTION OF THE VARIETY

Asexual reproduction of the new and distinct variety of peach tree was by budding to Nemaguard Rootstock (non-patented), as performed by us in our experimental orchard located near Modesto, Calif., and shows that all characteristics of the tree and its fruit run true to the original tree and are established and transmitted through succeeding asexual propagations.

SUMMARY OF THE VARIETY

The herein described new and distinct variety of peach tree is of large size, vigorous, upright growth and is a heavy and regular bearer of medium to large, yellow flesh, clingstone fruit with mild, sweet, sub-acid flesh, having excellent flavor and eating quality. The fruit is further characterized by having firm flesh with good handling and shipping quality, being relatively uniform in size throughout the tree, and having a high degree of attractive red skin color. In comparison to the May Crest, Fayette and Royal April peaches which have the normal commerical peach acidic flavor, the new variety has a sweet, mild, sub-acidic flavor similar to the Sweet Gem Peach (U.S. Palnt Pat. No. 7,952) and is approximately 22 days earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree as grown on Nemaguard rootstock (non-patented), its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Age.*—7 year old tree budded to Nemaguard Rootstock.

*Size.*—Large. Tree height at maturity pruned 12 to 14 feet in height and 12 to 14 feet in width for economical fruit harvesting.

*Vigor.*—Vigorous. Tree growth reaching 6 to 7 feet in height and 5 to 6 feet in width during the first growing season. During the first dormant season the tree is pruned 4 to 5 feet in height and primary scaffolds are selected to promote proper tree growth.

*Form.*—Upright. Usually pruned to vase shape.

*Productivity.*—Productive. Fruit set is twice or more of what is desirable for normal crop load. Fruit is thinned to desired numbers with proper spacing to develop marketable size. Number of fruit set per tree varies with climatic conditions during bloom time.

*Bearer.*—Regular. Amount of fruit thinned varies with the number of trees per acre, soil type, climatic conditions and cultural practices.

*Density.*—Medium dense. The number of branches and leaves that grow through the center of the tree restrict the amount of sunlight and air movement. Pruning to open the center of the tree (vase shape) is desirable to provide more sunlight to enhance the fruit color, increase soluble solids (Brix) and keep fruit wood healthy.

Trunk:

*Size.*—Large. Measured 16 inches in circumference at 16 inches above ground on a 7 year old tree.

*Texture.*—Medium shaggy.

*Color.*—Mouse gray to soot brown (5-E-3) to (5-E-5).

Branches:

*Size.*—Medium. Average circumference 8 inches, measured 36 inches above ground.

*Texture.*—Smooth to medium rough, varies with age of growth.

*Lenticels.*—Medium number. Large size, measured 36 inches above ground. Average length 7/32 inch. Average width 3/32 inch. Size decreases on smaller branches. Color—varies from golden brown to light brown (5-D-7) to (5-D-8).

*Color.*—Light brown to coffee brown (5-D-4) to (5-E-7), varies with age of growth.

Leaves:

*Size.*—Large. Average length 6½ inches. Average width 1¾ inches.

*Form.*—Lanceolate.

*Margin.*—Crenate.

*Thickness.*—Medium.

*Surface.*—Upper surface—relatively smooth, slightly indented over leaf veins, glabrous. Lower surface—relatively smooth, small ridges created with midrib and pinnate veining, glabrous.

*Petiole.*—Medium thickness. Medium length. Average length ½ inch. Average diameter 5/64 inch. Grooved longitudinally. Color—varies from pea green to light green (29-D-5) to (29-D-7).

*Glands.*—Number varies from 1 to 4. Average number 2. Medium size. Reniform. Positioned on base of leaf blade and upper portion of petiole. Average length 3/64 inch. Average diameter 2/64 inch. Color varies from spring green to yellowish green (30-C-6) to (30-C-8).

*Color.*—Upper surface—green to deep green (28-F-5) to (28-F-8). Lower surface—light green to grayish green (28-E-6) to (28-E-8).

Flower buds:

*Size.*—Medium to large. Average length ¾ inch. Average diameter 29/64 inch.

*Length.*—Medium.

*Form.*—Plump.

*Pubescence.*—Pubescent.

*Color.*—Light pink to pink (11-A-2) to (11-A-4), 4 days before bloom.

Flowers:

*Size.*—Large, showy. Average diameter 1 55/64 inches. Average height 51/64 inch.

*Pollen.*—Present, self-fertile. Color—pale yellow to yellow (3-A-2) to (3-A-4).

*Blooming period.*—Date of First Bloom Mar. 5, 1996. Date of Last Bloom Mar. 13, 1996. Varies slightly with climatic conditions.

*Stamens.*—Number per flower varies from 39 to 48, average number 44. Average filament length 31/64 inch. Filament color varies from white (14-A-1) to purplish white (14-A-3). Lighter color near anthers. Anther color—crimson red (11-A-8).

*Pistil.*—Normally 1, varies from 1 to 2. Average length 9/16 inch. Surface—pubescent. Height compared to stamens—slightly above, approximately 5/64 inch. Color varies from pale yellowish green to greenish white (30-A-2) to (30-A-4).

*Sepals.*—Number—5, alternately arranged to petals. Shape—slightly elongated, apex rounded. Pubescence—inner surface—glabrous. Outer surface—pubescent. Size—average length 11/64 inch. Average width 9/64 inch. Color—upper surface—grayish green to lettuce green (30-C-6) to (30-D-7). Lower surface magenta to dark magenta (13-E-8) to (13-F-8).

*Fragrance.*—Very slight.

*Color.*—Pink to light pink (11-A-2) to (11-A-3). Color fades with age of flowers.

*Petals.*—Nearly orbicular, slightly elongated. Narrows at point of attachment, edges slightly scalloped. Average length—11/16inch. Average width—45/64inch.

Fruit:

*Maturity when described.*—Firm ripe.

*Date of first picking.*—May 18, 1996.

*Date of last picking.*—May 24, 1996. Varies slightly with climatic conditions.

*Size.*—Medium to large. Average diameter axially 2⅞ inches. Average transversely in suture plane 2¾ inches. Average fruit weight 189 grams.

*Form.*—Nearly globose. Slightly flattened on stem end.

*Suture.*—Shallow, extends from base to apex.

*Ventral surface.*—Nearly rounded.

*Apex.*—Varies from nearly rounded to slight apical point.

*Base.*—Retuse.

*Cavity.*—*Rounded to slightly elongated in suture plane. Average depth*—⅜inch. Average breadth—¾inch.

Flesh:

*Ripens.*—Evenly.

*Texture.*—Firm.

*Fibers.*—Small, tender.

*Aroma.*—Moderate.

*Amygdalin.*—Undetected.

*Juice.*—Moderate amount, average. Brix 10.7°, sweet, sub-acid enhances flavor. Varies slightly with degree of ripeness.

*Eating quality.*—Excellent.

*Flavor.*—Excellent.

*Color.*—Light yellow to yellow (4-A-5) to (5-A-7). Pit cavity—yellow to yellowish gray (4-B-5) to (4-B-7).

Stem:

*Size.*—Length varies from 3/16 inch to ¼ inch. Diameter ⅛ inch. Enlarged at point of fruit attachment.

Skin:

*Thickness.*—Medium.

*Texture.*—Medium, tenacious to flesh.

*Down.*—Moderate, short.

*Tendency to crack.*—None.

*Color.*—Yellow to golden yellow ground color (4-A-6) to (5-A-7). Overspread with red to madder red (10-B-7) to (10-C-7).

Stone:

*Type.*—Clingstone.

*Size.*—Medium. Average length 1⅜ inches. Average width 1 inch. Average thickness ¾ inch.

*Form.*—Obovoid.

*Base.*—Rounded.

*Apex.*—Cuspidate.

*Surface.*—Irregularly furrowed toward apex, pitted toward base. Ridges relatively narrow and slightly sharp. Pits usually elongated, vary from elongated to round.

*Sides.*—Varies from equal to unequal. Some stones have one side extending a greater distance from suture plane.

*Tendency to split.*—Very slight.

*Color.*—Tan to light brown (5-C-5) to (5-D-5).

Use: Dessert. Market, local and long distance.

Keeping quality. Good—holds well in cold storage for 10 days and maintains good firmness and eating quality.

Shipping quality: Good—minimal bruising or scarring in packing and shipping trials.

Disease/resistance/susceptibility: No specific testing for relative plant/disease resistance/susceptibility has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics, with abnormal fungus, bacterial, virus, or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, and upright growth; being a regular and productive bearer of medium to large, early maturing, yellow flesh, sweet, sub-acid fruit with excellent flavor and eating quality; the fruit is further characterized by having an attractive red skin color, firm flesh with good handling and shipping quality, being relatively uniform in size throughout the tree; and, in comparison to the sub-acid yellow flesh Sweet Gem Peach (U.S. Plant Pat. No. 7,952), the new variety is approximately 22 days earlier in maturity.

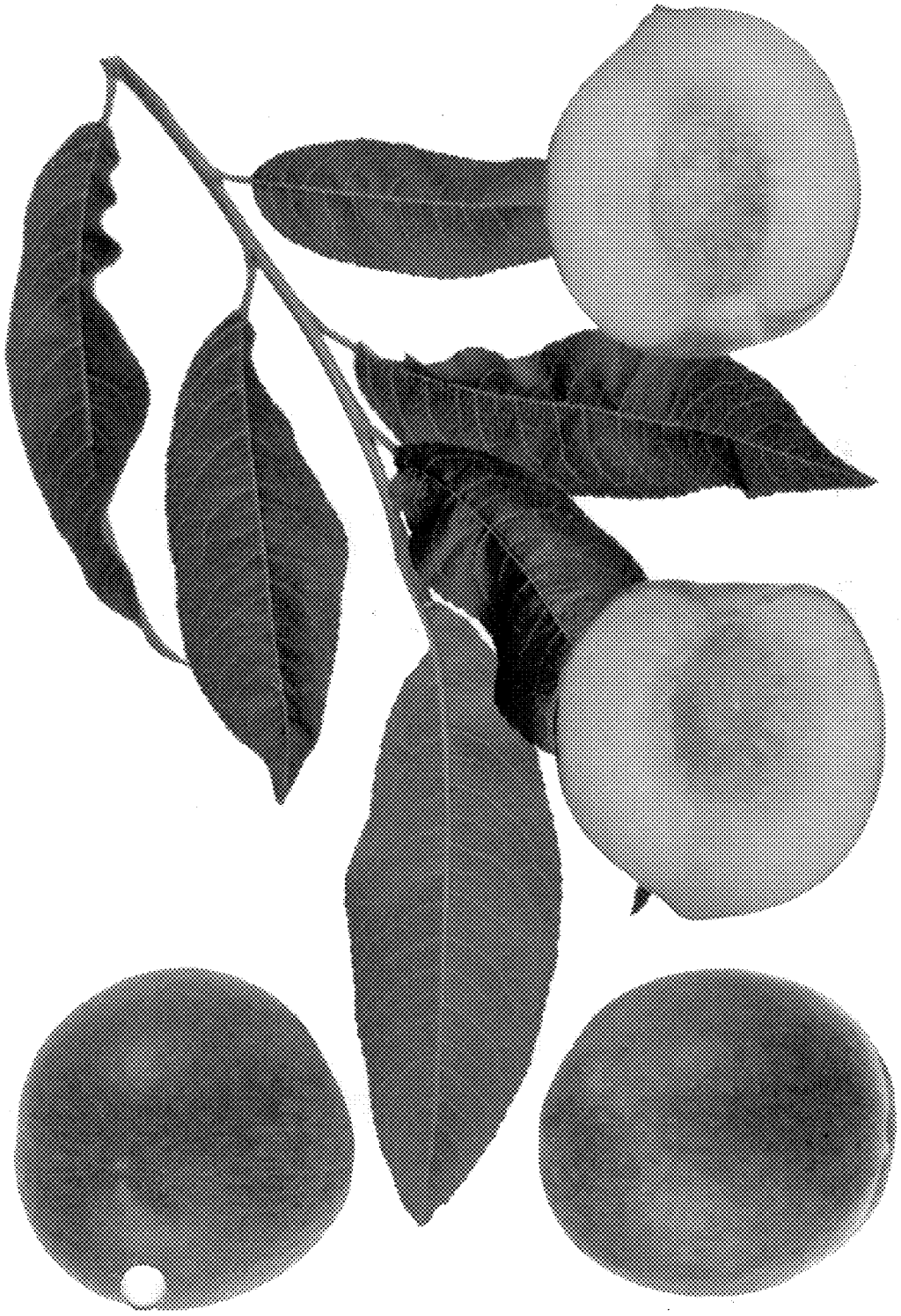

* * * * *